United States Patent [19]

Lui et al.

[11] Patent Number: 5,315,047

[45] Date of Patent: May 24, 1994

[54] PROCESS FOR THE PREPARATION OF HEXAFLUOROBUTANE, AND INTERMEDIATES THEREBY OBTAINABLE

[75] Inventors: Norbert Lui, Cologne; Albrecht Marhold, Leverkusen; Dietmar Bielefeldt, Ratingen, all of Fed. Rep. of Germany

[73] Assignee: Bayer Aktiengesellschaft, Leverkusen, Fed. Rep. of Germany

[21] Appl. No.: 48,103

[22] Filed: Apr. 15, 1993

[30] Foreign Application Priority Data

Apr. 29, 1992 [DE] Fed. Rep. of Germany ....... 4213975

[51] Int. Cl.$^5$ ..................... C07C 17/08; C07C 19/08
[52] U.S. Cl. .................................... 570/168; 570/166; 570/175; 570/176
[58] Field of Search ............... 570/175, 165, 166, 167, 570/168, 169, 176

[56] References Cited

U.S. PATENT DOCUMENTS

| | | | |
|---|---|---|---|
| 3,149,170 | 9/1964 | Clark et al. | 570/160 |
| 4,902,839 | 2/1990 | Bielefeldt et al. | |
| 4,954,666 | 9/1990 | Bielefeldt et al. | |
| 5,008,476 | 4/1991 | Manzer et al. | 570/166 |
| 5,146,019 | 9/1992 | Bielefeldt et al. | |
| 5,171,901 | 12/1992 | Gassen et al. | |
| 5,210,340 | 5/1993 | Bielefeldt et al. | |

FOREIGN PATENT DOCUMENTS

| | | |
|---|---|---|
| 0301346 | 2/1989 | European Pat. Off. |
| 0315783 | 5/1989 | European Pat. Off. |
| 0442075 | 8/1991 | European Pat. Off. |
| 0442087 | 8/1991 | European Pat. Off. |
| 1246703 | 8/1967 | Fed. Rep. of Germany |

OTHER PUBLICATIONS

*The Journal of Physical Chemistry*, vol. 83, No. 20; Oct. 4, 1979; pp. 5–12.

*Primary Examiner*—Alan Siegel
*Attorney, Agent, or Firm*—Sprung Horn Kramer & Woods

[57] ABSTRACT

1,1,1,4,4,4-Hexafluorobutane is prepared by first reacting 1,1,3,4,4-pentachlorobuta-1,3-diene with hydrogen fluoride in the presence of catalysts at 60° to 180° C. to give 1,1,1,4,4,4-hexafluoro-2-chlorobutane, and converting this to 1,1,1,4,4,4-hexafluorobutane. On working up the product of the first stage of the process, it is possible to isolate novel compounds of formula (I):

$$CF_2X-CH_2-R \qquad (I)$$

in which
X is fluorine or chlorine and
R is —CHCl—CF$_2$Cl, —CHCl—CFCl$_2$ or —CCl=CCl$_2$.

4 Claims, No Drawings

PROCESS FOR THE PREPARATION OF HEXAFLUOROBUTANE, AND INTERMEDIATES THEREBY OBTAINABLE

The present invention relates to a process for the preparation of hexafluorobutane from pentachlorobutadiene, which is readily available and ecologically harmless, and to intermediates which are obtainable by reacting pentachlorobutadiene with hydrogen fluoride.

Hexafluorobutane can be used as a propellant in the production of foams, thereby replacing the ecologically harmful chlorofluorocarbons.

It is known that hexafluorobutane can be obtained by first reacting hexachlorobutadiene with hydrogen fluoride in the presence of chlorine to give hexafluorodichlorobutene, and then hydrogenating the latter. This process has several disadvantageous aspects: hexafluorodichlorobutene and the hexafluoromonochlorobutene also formed in the first stage are highly toxic substances and therefore necessitate considerable safety precautions. Because of its possible carcinogenicity, the hexachlorobutadiene required as the starting material is no longer industrially available and can only be prepared at very great expense. Moreover, in this process, chlorine is initially introduced into a molecule and then has to be removed by hydrogenation.

Therefore there is still a need for a process for the preparation of hexafluorobutane in which readily available starting materials can be used and which proceeds via less toxic intermediates.

A process for the preparation of 1,1,1,4,4,4-hexafluorobutane has now been found which is characterised in that 1,1,3,4,4-pentachlorobuta-1,3-diene is first reacted with hydrogen fluoride in the presence of catalysts at 60° to 180° C. to give 1,1,1,4,4,4-hexafluoro-2-chlorobutane, and this is converted to 1,1,1,4,4,4-hexafluorobutane.

The 1,1,3,4,4-pentachlorobuta-1,3-diene (hereafter called pentachlorobutadiene) required as the starting material is readily available by the dimerisation of trichloroethylene and has a low toxicity.

In the first stage of the process according to the invention, pentachlorobutadiene is reacted with hydrogen fluoride in the presence of catalysts. In the process according to the invention, hydrogen fluoride is conveniently used in at least the stoichiometrically required amount, i.e. at least 6 mol of hydrogen fluoride per mol of pentachlorobutadiene. It is advantageous to use hydrogen fluoride in excess, for example 6.5 to 50 mol per mol of pentachlorobutadiene.

Lewis acids are particularly suitable catalysts for the process according to the invention. These can be e.g. metal and/or transition metal halides, especially metal and/or transition metal chlorides and fluorides. The following may be specifically mentioned: boron trifluoride, boron trichloride, antimony pentafluoride, antimony pentachloride, mixed antimony(V) fluorides and chlorides, titanium tetrachloride, tantalum pentachloride, tantalum pentafluoride, niobium pentachloride, niobium pentafluoride and tin tetrachloride. It is also possible to use mixtures of several catalysts.

The catalysts can optionally be used in a mixture with strong sulphonic acids, for example in a mixture with trifluoromethanesulphonic acid, chlorosulphonic acid and/or fluorosulphonic acid. Such mixtures can contain for example 0.05 to 50% by weight of strong sulphonic acids.

It is possible to use for example 0.05 to 30 mol % of catalysts, based on pentachlorobutadiene. This amount is preferably 0.1 to 20 mol %.

The first stage of the process according to the invention is carried out at temperatures of 60° to 180° C. This temperature is preferably 100° to 170° C.

The 1st stage of the process according to the invention is generally carried out in an autoclave under the autogenous pressure at the reaction temperature. The process can also be carried out at higher or lower pressures. Examples of possible pressures are those in the range whose lower limit is set by the fact that the hydrogen fluoride is in the liquid phase, and whose upper limit does not exceed 100 bar.

The hydrogen chloride formed can optionally be relieved through a pressure retaining valve.

The reaction temperature of the 1st stage of the process according to the invention can be maintained for example for 1 to 10 hours before the reaction mixture is cooled and worked up, for example by pouring on to ice and/or water, separation of the organic phase and distillation of the organic phase. Another possible working-up procedure is to distil off unconsumed hydrogen fluoride and then separate the remaining product mixture by distillation.

Apart from 1,1,1,4,4,4-hexafluoro-2-chlorobutane, one or more compounds of formula (I):

$$CF_2X—CH_2—R \qquad (I)$$

in which

X is fluorine or chlorine and

R is —CHCl—CF$_2$Cl, —CHCl—CFCl$_2$ or —CCl=CCl$_2$, can generally be isolated in the working-up of the reaction mixture of the 1st stage of the process according to the invention.

The compounds of formula (I) are especially 1,1,4,4,4-pentafluoro-1,2-dichlorobutane, 1,1,2-trichloro-4,4,4-trifluorobut-1-ene, 1,1,2,4-tetrachloro-4,4-difluorobut-1-ene and 1,1,2-trichloro-1,4,4,4-tetrafluorobutane.

The compounds of formula (I) can be recycled into another batch for the preparation of 1,1,1,4,4,4-hexafluoro-2-chlorobutane from pentachlorobutadiene and hydrogen fluoride, and thus can also be used for the preparation of 1,1,1,4,4,4-hexafluorobutane.

By-products which may be present in the reaction mixture from the reaction of pentachlorobutadiene with hydrogen fluoride, and which still have a lower degree of fluorination than the compounds of formula (I), can be recycled, either together with or separately from the compounds of formula (I), into another batch for the preparation of 1,1,1,4,4,4-hexafluoro-2-chlorobutane from pentachlorobutadiene and hydrogen fluoride.

The conversion of the 1,1,1,4,4,4-hexafluoro-2-chlorobutane obtained in the first stage of the process according to the invention to 1,1,1,4,4,4-hexafluorobutane (hereafter called hexafluorobutane) can be effected by means of elimination and hydrogenation, it being possible for the two steps to be carried out simultaneously or successively.

If it is desired to carry out the elimination and the hydrogenation successively, the elimination of hydrogen chloride to form 1,1,1,4,4,4-hexafluorobut-2-ene can be achieved for example by reacting the 1,1,1,4,4,4- hexafluoro-2-chlorobutane with an aqueous alkali solution. Examples of possible alkali solutions for this purpose are aqueous sodium hydroxide or potassium hydroxide solution in the concentration range from 10 to 50% by weight. The elimination can be carried out e.g. at temperatures in the range from −10° to +80° C. and with excess alkali solution, for example with 1 to 5 mol of alkali per mol of 1,1,1,4,4,4-hexafluoro-2-chlorobutane. The elimination can optionally be carried out in the presence of a solubiliser, e.g. an alcohol, or a phase transfer catalyst, e.g. a quaternary ammonium salt or a crown ether.

The hydrogenation of 1,1,1,4,4,4-hexafluorobut-2-ene to hexafluorobutane, which follows the elimination, can be effected in the liquid phase or in the gas phase. Possible catalysts are conventional hydrogenation catalysts, for example those containing palladium, nickel or compounds thereof. The hydrogenation can be carried out in a manner known per se, i.e. in the liquid phase with or without solvents, or in the gas phase with or without the addition of an inert gas.

The elimination and the hydrogenation are preferably carried out simultaneously, e.g. by passing 1,1,1, 4,4,4-hexafluoro-2-chlorobutane and hydrogen in the gas phase over a suitable catalyst in a fixed or fluidised bed, it being possible in this case for the molar ratio of 1,1,1,4,4,4-hexafluoro-2-chlorobutane to hydrogen to be for example 1:0.5 to 1:50. This molar ratio is preferably 1:1 to 1:20.

The combined elimination and hydrogenation can be carried out for example at normal pressure or at elevated pressures, for example in the range from normal pressure to 20 bar. It is preferably carried out at normal pressure.

Possible catalysts for this process are especially those containing transition metals on support materials. The preferred transition metals are palladium and platinum, especially palladium. The transition metals can optionally be doped with one or more other metals or metal compounds. Preferred doping materials are metals and metal compounds of elements of subgroups 1 to 8, especially titanium, zirconium, nickel, tantalum and silver and compounds thereof. Examples of support materials are activated charcoals, aluminium oxides, silicon dioxides, barium sulphate, spinels, silicates and titanium dioxide. Activated charcoals and lithium aluminium spinels are preferred. The catalysts can contain for example 0.5 to 30 g of transition metal per litre of support material. This content is preferably in the range from 2 to 20 g/l.

The flow rate of the reaction mixture and the amount of catalyst can be chosen for example so as to give catalyst loadings of 10 to 10,000 g/l×h, preferably 50 to 5000 g/l×h. The reaction temperatures are generally above 80° C. and preferably in the range from 100° to 350° C.

It is generally advantageous to condition freshly prepared catalysts before 1,1,1,4,4,4-hexafluoro-2-chlorobutane is passed over. The conditioning can be effected e.g. by heating the catalyst to a temperature in the range from 100° to 350° C. in a stream of nitrogen and, after some time, passing a nitrogen/hydrogen gas mixture over the heated catalyst, the proportion of hydrogen being increased continuously or stepwise until ultimately only hydrogen is passed over the heated catalyst. An alternative conditioning procedure is e.g. simply to heat the catalyst and pass hydrogen over.

The gas mixture obtained after the combined elimination and hydrogenation can be worked up for example by a procedure in which it is first scrubbed with water or dilute alkali solution to remove the hydrogen chloride formed, and the organic constituents of the reaction mixture are distilled, if appropriate after drying and/or cooling and/or phase separation. Traces of olefinic components in the hexafluorobutane can optionally be removed by oxidation, for example with potassium permanganate or chromates.

The process according to the invention makes it possible to prepare hexafluorobutane in an economically advantageous manner and with good yields and selectivities, while avoiding highly toxic starting materials and intermediates. This is extremely surprising since the large number of possible secondary reactions were such that this result could not be predicted. Particularly advantageous is the fact that the incompletely fluorinated products formed in the fluorination, especially the products of formula (I), can ultimately also be used to prepare hexafluorobutane by being recycled into the fluorination.

The following Examples illustrate the invention further. Where hydrogen fluoride has been used in these Examples, it is commercially available anhydrous hydrogen fluoride. The amounts given for hydrogen fluoride relate to measurements in the liquid phase.

EXAMPLES

Example 1

70 g of niobium pentachloride and 900 ml of hydrogen fluoride were placed in an autoclave. 450 g of pentachlorobutadiene were then added dropwise. The autoclave was closed and heated for 5 hours at 140° C. After cooling to room temperature, the reaction mixture was poured on to ice and the organic phase was separated off. Examination of the organic phase by gas chromatography showed that 100% of the pentachlorobutadiene had been converted. 80 g of 1,1,1,4,4,4-hexafluoro-2-chlorobutane, 190 g of 1,1,4,4,4-pentafluoro-1,2-dichlorobutane (boiling point 83.5° C. at normal pressure) and 80 g of lesser fluorinated products were isolated by fractional distillation of the organic phase. 1,1,4,4,4-pentafluoro-1,2-dichlorobutane and the lesser fluorinated products were added to the next batch.

Example 2

350 g of niobium pentachloride were placed in an autoclave and 950 ml of hydrogen fluoride were added in portions. 81 ml of fluorosulphonic acid and 800 g of pentachlorobutadiene were then added dropwise. The autoclave was closed and heated for 5 hours at 140° C., the hydrogen chloride formed being relieved at a pressure of 30 bar. After cooling to room temperature, the reaction mixture was poured on to ice and the organic phase was separated off.

Examination of the organic phase by gas chromatography showed that 100% of the pentachlorobutadiene had been converted. 320 g of 1,1,1,4,4,4-hexafluoro-2-chlorobutane and 30 g of 1,1,4,4,4-pentafluoro-1,2-dichlorobutane were isolated by distillation of the organic phase.

$^1$H and $^{19}$F NMR data of 1,1,4,4,4-pentafluoro-1,2-dichlorobutane: $^1$H NMR $\delta = 2.5-3.1$ (m, 2H, $CH_2$), 4.43 (dd, 1H, CH); $^{19}$F NMR $\delta = 61$ (dd, $CF_2Cl$), 64.7 (t, $CF_3$).

Example 3

150 ml of hydrogen fluoride were placed in an autoclave and 50 g of tantalum pentachloride were added. 100 g of pentachlorobutadiene were then added dropwise at 0° C. The reaction mixture was then heated for 5 hours at 140° C., the hydrogen chloride formed being relieved at a pressure of 30 bar. After cooling to room temperature, the reaction mixture was poured on to ice and the organic phase was separated off. 30 g of 1,1,1,4,4,4-hexafluoro-2-chlorobutane were isolated by distillation of the organic phase.

Example 4

960 ml of hydrogen fluoride were placed in an autoclave and 80 g of antimony pentachloride were addded. 450 g of pentachlorobutadiene were then added dropwise at 0° C. The reaction mixture was then heated for 5 hours at 150° C., the hydrogen chloride formed being relieved at a pressure of 40 bar. After cooling to room temperature, the reaction mixture was poured on to ice and the organic phase was separated off. 149 g of 1,1,1,4,4,4-hexafluoro-2-chlorobutane, 157 g of 1,1,4,4,4-pentafluoro-1,2-dichlorobutane and 21 g of lesser fluorinated products were isolated by distillation of the organic phase.

Example 5

40 g of antimony pentachloride were placed in an autoclave and 480 ml of hydrogen fluoride were added in portions. 11 ml of fluorosulphonic acid and 220 g of pentachlorobutadiene were then added dropwise. The autoclave was closed and heated for 5 hours at 140° C. After cooling to room temperature, the reaction mixture was poured on to ice and the organic phase was separated off. Examination of the organic phase by gas chromatography showed that 100% of the pentachlorobutadiene had been converted. The products isolated by distillation were 63 g of 1,1,1,4,4,4-hexafluoro-2-chlorobutane and 57 g of 1,1,4,4,4-pentafluoro-1,2-dichlorobutane.

Example 6

480 ml of hydrogen fluoride were placed in an autoclave and 40 g of antimony pentachloride were added. The autoclave was then closed and the mixture was heated for 5 hours at 60° C. After cooling to room temperature, 230 g of pentachlorobutadiene were added dropwise. The reaction mixture was then heated for 5 hours at 140° C. After cooling to room temperature, the reaction mixture was poured on to ice and the organic phase was separated off. 50 g of 1,1,1,4,4,4-hexafluoro-2-chlorobutane, 97 g of 1,1,4,4,4-pentafluoro-1,2-dichlorobutane and 14 g of lesser fluorinated products were isolated by distillation.

Example 7

18 g of antimony pentachloride were placed in an autoclave and 480 ml of hydrogen fluoride were added in portions. 220 g of pentachlorobutadiene were then added dropwise. The autoclave was closed and heated for 4 hours at 120° C. After cooling to room temperature, the reaction mixture was poured on to ice and the organic phase was separated off. Examination of the organic phase by gas chromatography showed that 100% of the pentachlorobutadiene had been converted. 14 g of 1,1,4,4,4-pentafluoro-1,2-dichlorobutane, 10 g of 1,1,2-trichloro-1,4,4,4-tetrafluorobutane, 75 g of 1,1,2-trichloro-4,4,4-trifluorobut-1-ene (boiling point 126° C. at normal pressure) and 10 g of lesser fluorinated products were isolated by distillation.

$^1$H and $^{19}$F NMR data of 1,1,2-trichloro-4,4,4-trifluorobut-1-ene: $^1$H NMR $\delta=3.42$ (q, J=9.4 Hz, 2H, CH$_2$); $^{19}$F NMR $\delta=64.73$ (t, J=9.4 Hz, CF$_3$).

$^1$H and $^{19}$F NMR data of 1,1,2-trichloro-1,4,4,4-tetrafluorobutane: $^1$H NMR $\delta=2.72$ (m, 1H, CH$_2$), 3.06 (m, 1H, CH$_2$), 4.58 (m, 1H, CHCl); $^{19}$F NMR $\delta=59.39$ (d, J=4.3 Hz, CFCl$_2$), 64.54 (t, J=9.7 Hz, CF$_3$).

Example 8

60 g of titanium tetrachloride and 1000 ml of hydrogen fluoride were placed in an autoclave. 500 g of pentachlorobutadiene were then added dropwise. The autoclave was closed and heated for 7 hours at 150° C. After cooling to room temperature, the reaction mixture was poured on to ice and the organic phase was separated off. 10 g of 1,1,1,4,4,4-hexafluoro-2-chlorobutane, 190 g of 1,1,4,4,4-pentafluoro-1,2-dichlorobutane, 60 g of 1,1,2-trichloro-4,4,4-trifluorobut-1-ene and 90 g of lesser fluorinated products were isolated by distillation of the organic phase.

Example 9

52 g of tin tetrachloride, 900 ml of hydrogen fluoride and 450 g of pentachlorobutadiene were introduced into an autoclave and then heated for 5 hours at 140° C. After cooling to room temperature, the reaction mixture was poured on to ice and the organic phase was separated off. 230 g of 1,1,2-trichloro-4,4,4-trifluorobut-1-ene and 139 g of 1,1,2,4-tetrachloro-4,4-difluorobut-1-ene (boiling point 45.5°–46° C./12 mbar) were isolated by distillation of the organic phase.

$^1$H and $^{19}$F NMR data of 1,1,2,4-tetrachloro-4,4-difluorobut-1-ene: $^1$H NMR $\delta=3.64$ (t, J=12 Hz, CH$_2$); $^{19}$F NMR $\delta=50.28$ (t, J=12 Hz, CF$_2$Cl).

Example 10

20 g of boron trifluoride, 480 ml of hydrogen fluoride and 230 g of pentachlorobutadiene were introduced into an autoclave and then heated for 5 hours at 150° C. After cooling to room temperature, the reaction mixture was poured on to ice and the organic phase was separated off. 80 g of 1,1,2,4-tetrachloro-4,4-difluorobut-1-ene, 9 g of 1,1,2-trichloro-4,4,4-trifluorobut-1-ene, 60 g of pentachlorobutadiene and 22 g of lesser fluorinated products were isolated after distillation of the organic phase.

Example 11

10 g of antimony pentafluoride were placed in an autoclave and 200 ml of hydrogen fluoride were added in portions. 110 g of pentachlorobutadiene were then added dropwise. The autoclave was closed and heated for 5 hours at 140° C. After cooling to room temperature, the reaction mixture was poured on to ice and the organic phase was separated off. Examination of the organic phase by gas chromatography showed that 100% of the pentachlorobutadiene had been converted. 19 g of 1,1,1,4,4,4-hexafluoro-2-chlorobutane, 55 g of 1,1,4,4, 4-pentafluoro-1,2-dichlorobutane and 11 g of lesser fluorinated products were isolated by distillation of the organic phase.

Examples 12 and 13

A vertical, electrically heated tubular reactor made of quartz (length 310 mm, diameter 36 mm) was charged with 200 ml of a supported catalyst containing 18 g of palladium per litre of a lithium aluminium spinel in the form of spheres (sphere diameters 3 to 5 mm). The catalyst was conditioned for 6 hours at 200° C. while 20 to 25 ml of hydrogen was passed through per hour. The two hydrogenations described below were then carried out. The gases leaving the quartz tube were condensed at −78° C. and examined by $^{19}F$ NMR spectroscopy and by GC coupled with MS.

Example 12

Amounts used: 0.06 mol of 1,1,1,4,4,4-hexafluoro-2-chlorobutane and 0.3 mol of hydrogen
  Reaction conditions: 200° C., normal pressure
  Catalyst loading: 300 g/l×h
Hexafluorobutane was obtained with a conversion of 90% and a selectivity of 92%.

Example 13

Amounts used: 0.15 mol of 1,1,1,4,4,4-hexafluoro-2-chlorobutane and 0.9 mol of hydrogen
  Reaction conditions: 300° C., normal pressure
  Catalyst loading: 300 g/l×h
Hexafluorobutane was obtained with a conversion of 92% and a selectivity of 83%.

Example 14

The process was carried out in the same apparatus as in Examples 12 and 13, but the catalyst used was activated charcoal in the form of spheres containing 5 g of palladium per litre. The catalyst was conditioned by a procedure in which it was heated to 235° C. and a stream of nitrogen of 100 ml/h was initially passed over for 1 hour. Nitrogen/hydrogen mixtures were then passed over the catalyst in an amount of 100 ml/h in each case and for 30 minutes in each case, the hydrogen content of the mixtures being increased in four stages from 4:1 through 3:2 and 2:3 to 1:4 parts by volume. Finally, 50 ml of hydrogen were passed over the catalyst at 235° C. over a period of 30 minutes.

The combined elimination and hydrogenation according to the invention was then carried out as follows:
  Amounts used: 1.5 mol of 1,1,1,4,4,4-hexafluoro-2-chlorobutane and 4.0 mol of hydrogen
  Reaction conditions: 300° C., normal pressure
  Catalyst loading: 300 g/l×h
Hexafluorobutane was obtained with a conversion of more than 99.5% and a selectivity of more than 99%.

Example 15

The procedure was as in Example 14, except that the catalyst was not conditioned.
  Amounts used: 0.2 mol of 1,1,1,4,4,4-hexafluoro-2-chlorobutane and 2.5 mol of hydrogen
  Reaction conditions: 250° C., normal pressure
  Catalyst loading: 200 g/l×h
Hexafluorobutane was obtained with a conversion of 83% and a selectivity of 94.8%.

What is claimed is:

1. A process for the preparation of 1,1,1,4,4,4-hexafluorobutane, in which 1,1,3,4,4-pentachlorobuta-1,3-diene is first reacted with at least 6 mols of hydrogen fluoride per mol of pentachlorobutadiene in the presence of a Lewis acid catalyst at 60° to 180° C. to give 1,1,1,4,4,4-hexafluoro-2-chlorobutane, and converting said 1,1,1,4,4,4-hexafluoro-2-chlorobutane to 1,1,1,4,4,4-hexafluorobutane by means of elimination and hydrogenation.

2. The process of claim 1, in which the Lewis acid is used in a mixture with a strong sulphonic acid.

3. The process of claim 1, in which the catalyst used is one containing a transition metal on a support material.

4. The process of claim 1, in which the reaction temperature is above 80° C.

* * * * *